US006402320B1

(12) United States Patent
Borchert

(10) Patent No.: US 6,402,320 B1
(45) Date of Patent: Jun. 11, 2002

(54) METHODS AND APPARATUS FOR MEASURING VISUAL ACUITY IN PREVERBAL CHILDREN

(75) Inventor: Mark S. Borchert, La Canada, CA (US)

(73) Assignee: Childrens Hospital Los Angeles, Los Angeles, CA (US)

( * ) Notice: Subject to any disclaimer, the term of this patent is extended or adjusted under 35 U.S.C. 154(b) by 148 days.

(21) Appl. No.: 09/612,903

(22) Filed: Jul. 10, 2000

Related U.S. Application Data

(60) Provisional application No. 60/147,960, filed on Aug. 9, 1999.

(51) Int. Cl.[7] .............................. A61B 3/02; A61B 3/14
(52) U.S. Cl. ...................................... 351/224; 351/209
(58) Field of Search ............................... 351/209, 210, 351/224, 226, 237, 238, 239, 240, 243; 345/156, 158, 700

(56) References Cited

U.S. PATENT DOCUMENTS 6,106,119 A * 8/2000 Edwards ..................... 351/209
6,243,076 B1 * 6/2001 Hatfield ...................... 345/146

OTHER PUBLICATIONS

Velma Dobson; 20. Visual Acuity Testing in Infants: From Laboratory to Clinic, *Abnormal Visual Development*, pp. 318–334.

*ISCAN Marketing Materials*; pp. 2–20.
*Eye Movement Equipment Database*, 3 pgs. ( This document is maintained by the Eye Movement Equipment Database Manager Last modified 9th Jan. 1998).
*The Eyegaze System™ For the Physically Disabled*, LC Technologies, Inc., 10 pgs.

* cited by examiner

Primary Examiner—Geroge Manuel
(74) Attorney, Agent, or Firm—Myers Bigel Sibley & Sajovec

(57) ABSTRACT

An automated method of measuring visual acuity utilizing an electronic visual display comprises the steps of: (a) presenting a fixation target for attracting a subject's attention on said electronic visual display; then (b) presenting a test screen on said electronic visual display, wherein said test screen comprises at least two separate fields, with one of said fields containing a first test pattern and another of said fields containing a control pattern; wherein said test pattern is configured to stimulate eye movement by said subject when said pattern is recognizable by said subject; then (c) detecting whether or not eye movement to said test pattern occurs, the presence of eye movement to said test pattern confirming the discernability of said first test pattern by said subject; and then (d) repeating steps (b) and (c) above with at least one subsequent test pattern, wherein said subsequent test pattern is more difficult to discern than said first test pattern; and then (e) determining said subject's visual acuity from the presence or absence of detected eye movement to said first test pattern and said at least one subsequent test pattern. Methods of measuring peripheral vision and apparatus for carrying out the foregoing methods are also disclosed.

15 Claims, 3 Drawing Sheets

Figure 1: Flow Chart for the Eye Tracker
<u>Iterative Test</u>: Keep reducing the size of the grating until the child is no longer looking at the grating; eye movement is random. Entire Test only takes 30 seconds.
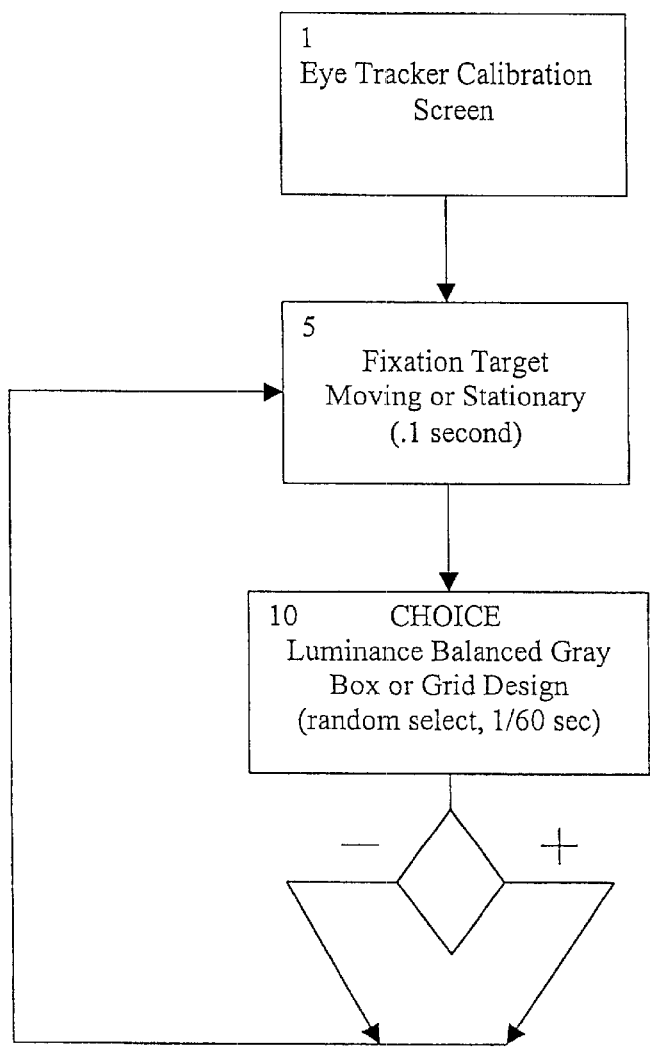

Figure 2: Flow Chart for the Peripheral Vision Tester
Test: Peripheral Target continues to move until the test subject recognizes it.
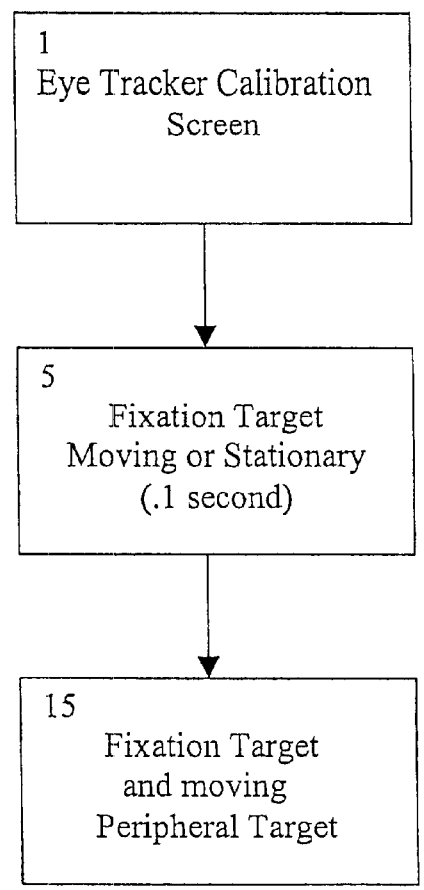

Figure 3: Block Diagram of the Apparatus for Measuring Visual Acuity
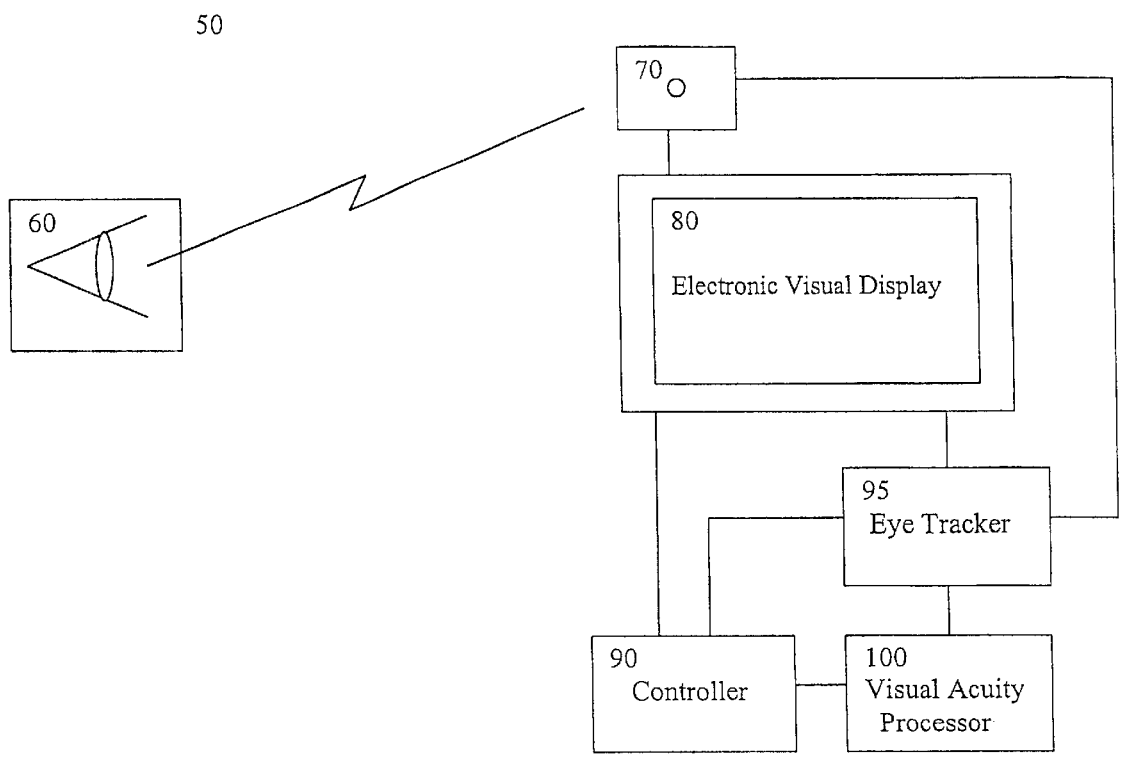

METHODS AND APPARATUS FOR MEASURING VISUAL ACUITY IN PREVERBAL CHILDREN

RELATED APPLICATIONS

This application claims priority from U.S. Provisional Application Ser. No. 60/147,960, filed Aug. 9, 1999, the disclosure of which is incorporated by reference herein in its entirety.

FIELD OF THE INVENTION

The present invention concerns methods and apparatus for measuring visual acuity in preverbal children, along with methods and apparatus for measuring peripheral vision.

BACKGROUND OF THE INVENTION

Webster's Dictionary defines visual acuity as the relative ability of the visual organ to resolve detail; keenness of perception. For adults, acuity is tested very easily using an eye chart and the results are given in the form X/X, for example 20/20. However, there is no good way to measure visual acuity in preverbal children. Knowledge of a child's acuity is important because children learn using their senses and if they cannot see well this will hinder their development. Therefore, it is important to know if the infant's vision is impaired as early as possible. Tests that measure visual acuity in preverbal children do exist, the most effective of which is the Forced Preferential Looking Test (the Keller Acuity Test). This procedure is discussed in *Visual Acuity Testing in Infants: From Laboratory to Clinic* by Velma Dobson.

This procedure involves presenting the child with a series of gray cards, each 25.5×51.0 cm. Each card contains a 12.5×12.5 cm square patch of black and white grating located to the left or right of a small, 4 mm diameter, central aperture. The spatial frequency varies from card to card, from 0.23 to 38 cycles/cm. During testing, cards are placed face-down on a table beside the tester, arranged in order of increasing spatial frequency. The tester, who does not know whether the grating is located on the left or the right side of each card, watches the infant's eye and head movements during repeated presentations of each card. Based on the infant's looking behavior, the tester decides which cards contain gratings that can be resolved by the infant. Cards for which the infant shows consistent looking behavior are judged to contain gratings the infant can resolve. Cards that do not elicit consistent looking behavior are judged to contain gratings that can not be resolved by the infant. Acuity is estimated as the spatial frequency of the finest grating the tester judges the infant can resolve. This test is fairly short, average test duration is 3–5 minutes for normal infants and young children 4 weeks to 36 months of age and approximately 8 minutes for infants with eye disorders.

The acuity card procedure has many limitations. First, the accuracy of acuity measurements can vary to a great degree and retests are often necessary to obtain accurate results. Second, the results of the test may be skewed by the potential bias of the tester. The tester may be familiar with the infant's history and make assumptions before the test is given which are reflected in the test results. Third, since the acuity card test is conducted at close distances, it is less sensitive to myopic refractive errors than are the 10- and 20-feet picture and letter acuity tests used with older children and adults. Myopia is a condition in which the visual images come to a focus in front of the retina of the eye resulting especially in defective vision of distant objects. Finally, the lack of durability of the cards can contribute to the inaccuracy of the test. This is due the fact that the face of the card should appear uniformly gray when the grating cannot be resolved. Blemishes on the card can produce consistent looking behavior by the patient which could be interpreted by the tester as recognition of the grating. Accordingly, there continues to be a need for improved methods of testing visual acuity in preverbal children.

SUMMARY OF THE INVENTION

A first aspect of the present invention is an automated method of measuring visual acuity utilizing an electronic visual display. The method comprises the steps of:

(a) presenting a fixation target for attracting a subject's attention on said electronic visual display; then (b) presenting a test screen on said electronic visual display, wherein said test screen comprises at least two separate fields, with one of said fields containing a first test pattern and another of said fields containing a control pattern; wherein said test pattern is configured to stimulate eye movement by said subject when said pattern is recognizable by said subject; then (c) detecting whether or not eye movement to said test pattern occurs, the presence of eye movement to said test pattern confirming the discernability of said first test pattern by said subject; and then (d) repeating steps (b) and (c) above with at least one subsequent test pattern, wherein said subsequent test pattern is different from (e.g., more or less difficult to discern) said first test pattern; and then (e) determining said subject's visual acuity from the presence or absence of detected eye movement to said first test pattern and said at least one subsequent test pattern.

A second aspect of the invention is an automated method of measuring the quality of peripheral vision utilizing an electronic visual display. The method comprises the steps of:

(a) presenting a fixation target for attracting a subject's attention on said electronic visual display; then (b) presenting a peripheral target on a substantially semicircular path, wherein said semicircular path has a first endpoint, a second endpoint, and a center point overlying said fixation target, and wherein said peripheral target is presented at various spaced apart positions along said path, and wherein said peripheral target is configured to stimulate eye movement confirming the recognition of said peripheral target by said subject; then (c) detecting whether or not eye movement to said peripheral target occurs, the presence of eye movement to said peripheral target confirming the recognition of said peripheral target by said subject; and then (d) determining said subject's peripheral vision quality from the point on said semicircular path where the presence of eye movement was detected.

Apparatus for carrying out the foregoing methods are also disclosed herein.

BRIEF DESCRIPTION OF THE DRAWINGS

FIG. 1 is a flow chart illustrating the steps involved in practicing the claimed invention in relation to visual acuity.

FIG. 2 is a flow chart illustrating the steps involved in practicing the claimed invention in relation to peripheral vision.

FIG. 3 is a block diagram illustrating the Apparatus for Measuring Visual Acuity.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Referring to FIGS. 1 and 3. FIG. 1 is a flow chart which illustrates the steps involved practicing the present invention. FIG. 3 is a block diagram of the apparatus for measuring visual acuity 50. In particular, block 1 is the eye tracker calibration screen of an eye tracking calibration device. This is a known device for tracking where the eye 60 is looking on a screen. It accomplishes this task using a eye tracking camera 70, typically attached to the display, that tracks where the eye 60 is looking. Several companies manufacture such products. One such is LC Technologies, Inc. of Alexandria, Va., but any suitable eye tracker 95 may be used to provide the means for monitoring where the test subject is looking on an electronic visual display 80. This electronic visual display 80 can be a computer monitor, a television set, a movie screen, a head set or any number of other devices that would accomplish the same end. The eye tracker camera can also be attached to a head set.

Block 5 represents the fixation target. The fixation target is presented on the electronic visual display 80 to attract the test subjects eyes to it. The fixation target is displayed for a duration of approximately 1 second and could be in motion or stationary. Next, illustrated in block 10, a test screen is presented on the electronic visual display. The test screen comprises two separate fields. One field contains a first test pattern and the other field contains a control pattern. The preferred embodiments of the first test pattern and the control pattern are preferably a luminance balanced grid design and gray box, respectively. These patterns could take on many different forms and should not be construed as limited to these embodiments. Next, the eye tracker 95 detects where the test subject is looking (which takes about $\frac{1}{60}^{th}$ of a second). If the test subject can distinguish between the test pattern and the control pattern (i.e., by looking at the test pattern), the test pattern is automatically replaced with a subsequent test pattern which is more difficult to discern than the first. For example, if the test pattern is in the form of a luminance balanced grid design, the first test pattern is automatically replaced with a subsequent pattern that has gratings of increased spatial frequency. This is an iterative process (repeating blocks 5 and 10 as shown in FIG. 1) which terminates when it appears that the test subject can no longer distinguish between the test pattern and the control pattern (i.e., is looking randomly at either of the two patterns). Of course, the different patterns could be presented randomly, or presented in a bracketing or "enveloping" manner, etc. The manner of presentation is determined by a controller 90 from the fact that the test subject is not looking at a particular spot, but is randomly glancing around the room. The whole test preferably lasts for no more than 1, 2, or 3 minutes, and preferably lasts approximately thirty seconds. Preferably, subsequent test patterns are presented randomly on the different fields.

After the test is completed, the test subject's visual acuity is determined by a visual acuity processor 100. The visual acuity processor 100 determines the subject's visual acuity by evaluating the least discernable test target seen by the test subject. The means used for determining the test subject's visual acuity can be accomplished in many different ways. A computer algorithm could be implemented to determine the infant's visual acuity from the test results, the tester could determine it himself, or the results could be evaluated in many other different ways.

The test patterns may be presented to one eye at a time by optical filtering. It is possible to test both eyes of the test subject simultaneously with polarized glasses and a polarized screen. This is possible because the child does not know which eye it is looking with. This method is preferred to covering the child's eye with an object or hand because the child may be irritated by this. A polarized screen can be implemented by having the top half of the screen polarized one way and the bottom half of the screen polarized the other way, and the attractor target moving up or down. Or, the screen can be alternately electrically polarized from one screen or frame to the next as different patterns are presented.

Referring now to FIG. 2, it is also possible to monitor the test subject's peripheral vision. The process is similar to the previously described process except in block 15 there is a fixation target on the electronic visual display and a peripheral target in motion. The fixation target keeps the test subject's eyes looking forward while the peripheral target slowly moves around from one endpoint of a semicircular path (180 degrees) towards the center of the semicircle. The peripheral target continues to move until the test subject notices the peripheral target. Alternatively, and preferably, the peripheral target is presented as a set of different targets at spaced-apart locations along the path, which targets may be varied at each location by size, intensity, or both. The eye tracker 95 monitors the test subject's eye movement for recognition of the peripheral target and marks the recognition point on the semicircular path. This mark represents the quality of the test subject's peripheral vision. This can be done for both eyes by starting at one endpoint of the semicircle for the right eye and the opposite endpoint of the semicircle for the left eye.

According to the methods of the present invention, the visual acuity of a preverbal child can be tested faster and more accurately than ever before. More particularly, this method decreases the testing time from about five minutes to not more than 1, 2 or 3 minutes.

In the drawings and specification, there have been disclosed typical preferred embodiments of the invention and, although specific terms are employed, they are used in generic and descriptive sense only and not for the purposes of limitation, the scope of the invention being set forth in the following claims.

That which is claimed is:

1. An automated method of measuring visual acuity utilizing an electronic visual display, said method comprising the steps of:

(a) presenting a fixation target for attracting a subject's attention on said electronic visual display; then (b) presenting a test screen on said electronic visual display, wherein said test screen comprises at least two separate fields, with one of said fields containing a first test pattern and another of said fields containing a control pattern; wherein said test pattern is configured to stimulate eye movement by said subject when said pattern is recognizable by said subject; then (c) detecting whether or not eye movement to said test pattern occurs, the presence of eye movement to said test pattern confirming the discernability of said first test pattern by said subject; and then (d) repeating steps (b) and (c) above with at least one subsequent test pattern, wherein said subsequent test pattern is more or less difficult to discern than said first test pattern; and then (e) determining said subject's visual acuity from the presence or absence of detected eye movement to said first test pattern and said at least one subsequent test pattern.

2. An automated method according to claim 1, wherein said repeating step (d) is carried out until said detected eye movement is occurring essentially randomly, whereupon step (e) is initiated.

3. A automated method according to claim 1, wherein said test pattern and said control pattern are luminance balanced.

4. An automated method according to claim 3, wherein said control pattern is a gray field.

5. An automated method according to claim 1, wherein said first test pattern and said at least one subsequent test pattern are gratings of successively decreasing spatial frequency.

6. An automated method according to claim 1, wherein said fixation target is in motion.

7. An automated method according to claim 1, wherein said fixation target is stationary.

8. An automated method according to claim 1, wherein said test pattern is presented to one eye at a time by optical filtering.

9. An apparatus for measuring visual acuity utilizing an electronic visual display, the apparatus comprising:

(a) a fixation target for attracting a subject's attention on said electronic visual display;

(b) a test screen on said electronic visual display, wherein said test screen comprises at least two separate fields, with one of said fields containing a first test pattern and another of said fields containing a control pattern; wherein said test pattern is configured to stimulate eye movement by said subject when said pattern is recognizable by said subject;

(c) an eye tracker that detects whether or not eye movement to said test pattern occurs, the presence of eye movement to said test pattern confirming the discernability of said first test pattern by said subject; and then (d) a controller configured that repeats steps (b) and (c) above with at least one subsequent test pattern, wherein said subsequent test pattern is more difficult to discern than said first test pattern; and then (e) a visual acuity processor that determines said subject's visual acuity from the presence or absence of detected eye movement to said first test pattern and said at least one subsequent test pattern.

10. An apparatus according to claim 9, wherein said controller configured for repeating step (d) is carried out until said detected eye movement is occurring essentially randomly, whereupon step (e) is initiated.

11. A apparatus according to claim 9, wherein said test pattern and said control pattern are luminance balanced.

12. An apparatus according to claim 9, wherein said control pattern is a gray field.

13. An apparatus according to claim 9, wherein said first test pattern and said at least one subsequent test pattern are gratings of successively decreasing spatial frequency.

14. An automated method of measuring the quality of peripheral vision utilizing an electronic visual display, said method comprising the steps of:

(a) presenting a fixation target for attracting a subject's attention on said electronic visual display; then (b) presenting a peripheral target on a substantially semicircular path, wherein said semicircular path has a first endpoint, a second endpoint, and a center point overlying said fixation target, and wherein said peripheral target is presented at spaced apart locations along said path, and wherein said peripheral target is configured to stimulate eye movement confirming the recognition of said peripheral target by said subject; then (c) detecting whether or not eye movement to said peripheral target occurs, the presence of eye movement to said peripheral target confirming the recognition of said peripheral target by said subject; and then (d) determining said subject's peripheral vision quality from the point on said semicircular path where the presence of eye movement was detected.

15. An apparatus for measuring the quality of peripheral vision utilizing an electronic visual display, said apparatus comprising:

(a) a fixation target for attracting a subject's attention on said electronic visual display;

(b) a peripheral target on a semicircular path, wherein said semicircular path has a first endpoint, a second endpoint, and a center point, and wherein said peripheral target is presented at spaced apart locations along said path, and wherein said peripheral target is configured to stimulate eye movement confirming the recognition of said peripheral target by said subject;

(c) means for detecting whether or not eye movement to said peripheral target occurs, the presence of eye movement to said peripheral target confirming the recognition of said peripheral target by said subject; and (d) means for determining said subject's peripheral vision quality from the point on said semicircular path where the presence of eye movement was detected.

* * * * *